United States Patent [19]

Rommel

[11] 4,015,199
[45] Mar. 29, 1977

[54] CELL FOR MEASUREMENT OF THE ELECTRICAL CONDUCTIVITY OF LIQUIDS

[75] Inventor: Klaus Rommel, Jona, Switzerland

[73] Assignee: Zellweger, Ltd., Switzerland

[22] Filed: Oct. 29, 1975

[21] Appl. No.: 627,020

[30] Foreign Application Priority Data

Nov. 14, 1974 Switzerland ............. 15176/74

[52] U.S. Cl. ...................... 324/30 B; 324/64
[51] Int. Cl.² ......................... G01N 27/42
[58] Field of Search ........... 324/30 R, 30 B, 11, 324/64; 204/195 R, 195 F

[56] References Cited

UNITED STATES PATENTS

| | | | |
|---|---|---|---|
| 2,793,527 | 5/1957 | Turner, Jr. et al. | 324/30 B |
| 3,134,077 | 5/1964 | Hutchins et al. | 324/64 |
| 3,207,981 | 9/1965 | Marsh et al. | 324/64 |
| 3,781,660 | 12/1973 | Ludt | 324/30 B |

FOREIGN PATENTS OR APPLICATIONS 301,674  4/1968  Sweden ............. 324/30 B

Primary Examiner—R. V. Rolinec
Assistant Examiner—Michael J. Tokar
Attorney, Agent, or Firm—Craig & Antonelli

[57] ABSTRACT

A cell for the measurement of electrical conductivity of liquids by the principle of the four electrode measuring technique in which two current electrodes are spaced from one another and voltage electrodes provide a voltage tap-off. The voltage electrodes include at least two voltage electrodes associated with each current electrode and electrically connected in parallel. The at least two voltage electrodes are disposed along an equipotential line around a current electrode at positions on the equipotential line which exhibit low current density.

10 Claims, 5 Drawing Figures

CELL FOR MEASUREMENT OF THE ELECTRICAL CONDUCTIVITY OF LIQUIDS

The present invention relates to cells for measurement of the electrical conductivity of liquids and in particular of those liquids which are polluted and tend to form sediments.

Measuring cells are used for the measurement of the electrical conductivity of liquids, which cells in their simplest form consist of two electrodes spaced from each other at a defined distance. The measurement is carried out in such a way that the measuring cell is immersed in the liquid to be examined, an alternating voltage is applied and the resistance between the electrodes is measured. This arrangement in various applications conceals within it two basic sources of error, namely, a polarization at the electrodes and a change in the cell constants by pollution.

Polarization makes the conductivity appear lower. While, it is true that its effect diminishes with increasing measuring frequency, the measuring frequency cannot be selected as high as is desirable for other reasons (cable capacitance, cell capacitance).

Measuring cells with four electrodes offer an alternative. In this case, the alternating voltage is fed through two current electrodes and two voltage electrodes tap off a partial voltage which is proportional to the conductivity. In order to exploit the basic advantage of this arrangement, two requirements must be met:

1. an amplifier with high-Z input resistance must be connected to the voltage electrodes, so that no significant current can flow through these electrodes;
2. the voltage electrodes must be arranged in such a way that they are at a point where the current density is as low as possible.

This permits the voltage electrodes to have a similarly large area in comparison with the current electrodes, without forming a noticeable shunt to the liquid. If the voltage electrodes are point-shaped, the slightest pollution will put the cell out of action. However, if an electrode with a large surface area forms a metallically highly conductive parallel resistance to the liquid, the current flows through it and a secondary polarization occurs at the voltage electrodes. Various types of measuring cell in which attempts have been made to solve these problems have already been proposed.

It is an object of the present invention to provide an improvement in measuring cells for the measurement of the electrical conductivity of liquids with regard to sources of error as a result of pollution, without tolerating disruptive polarization.

In a measuring cell according to the present invention, a voltage tap-off is effected through at least two parallel connected partial electrodes which are each located on an equipotential line around each current electrode and in addition only such positions are occupied on the equipotential line as exhibit a low current density.

These and other objects, features and advantages of the present invention will become more apparent from the following description when taken in connection with the accompanying drawings, which show for purposes of illustration only, one embodiment in accordance with the present invention, and wherein.

Figure 1:
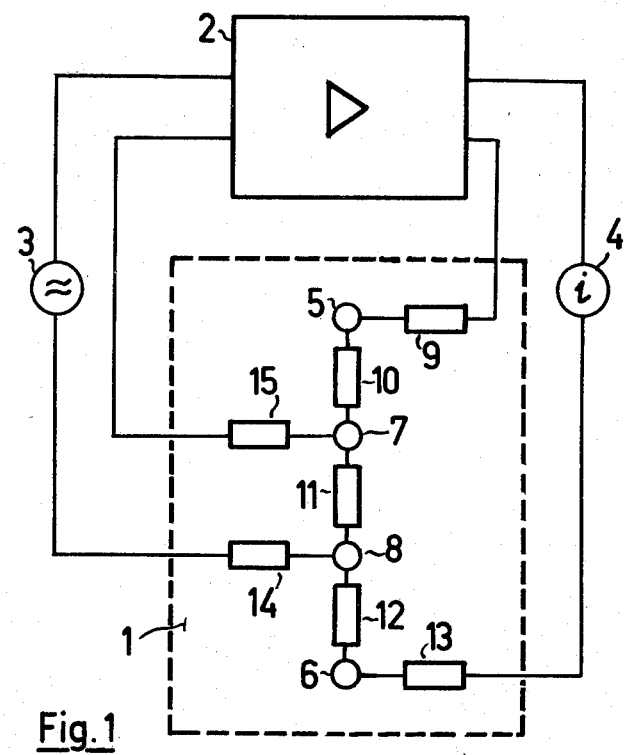
FIG. 1 is an equivalent circuit diagram of a measuring cell with associated measurement set-up.

Referring now to the drawings wherein like reference numerals designate like parts throughout the several figures, there is shown in FIG. 1 a schematic arrangement of a four electrode measuring system consisting of the measuring cell, which is shown as electrical equivalent circuit diagram 1, a high-Z amplifier 2 and a measurement voltage source 3. The resulting measurement value is displayed on an indicator 4. The measuring cell comprises current electrodes 5 and 6 and voltage electrodes 7 and 8. The voltage drop is measured across the resistance 11 by means of the amplifier 2, while partial resistances 10 and 12 are determined by the geometrical distance from the voltage electrodes 7, 8 to the current electrodes 5, 6.

Fundamentally, two types of pollution must be considered. One type is pollution of the cell which still leaves the entire surface of the electrodes in conductive contact with the liquid and forms additional resistances 9, 13, 14, 15. Resistances 14 and 15, particularly, can assume high values without causing an impermissibly high measurement error, because the input resistance of the amplifier 2 can as a pre-requisite be designed to be very high.

A second type is pollution of the electrodes wherein a partial, non-conductive encrustation of the electrodes shifts the mean distances of the electrodes towards one another. Thus, the ratio of the resistance values of resistance 11 to that of the resistances 10, 12 is changed and also the cell constant is changed.

In a known arrangement, it has been proposed to effect the voltage tap-off with two pairs of electrodes and in this way to achieve a reduction of susceptibility to pollution. However, the electrodes in this proposal are arranged in a line, so that the voltage electrodes are located in the area of the greatest current density.

Figure 2:
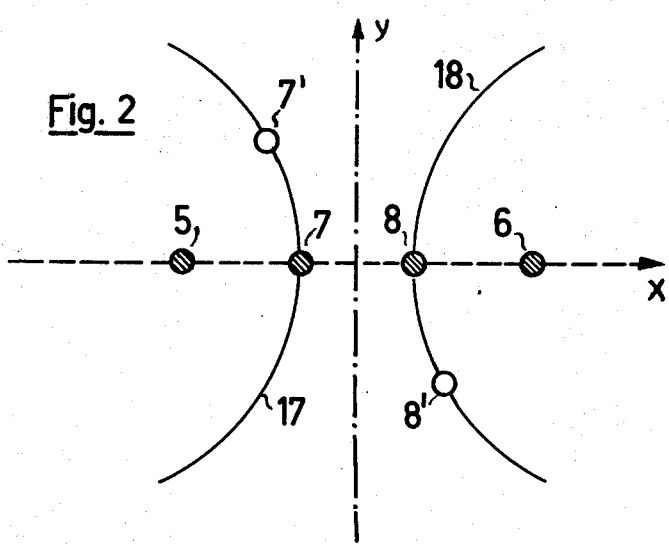
FIG. 2 illustrates the principle of the geometrical arrangement of the electrodes of the cell.

The principle of the geometric arrangement of the present invention is illustrated in FIG. 2. The voltage electrodes 7 and 8 are located between the current electrodes 5 and 6. In so doing, the voltage electrodes 7 and 8 are moved away from the current electrodes in such a way that they are situated in the flattest part of the potential flow between the current electrodes 5 and 6. They then only tap off a small part in the almost linear area of the potential flow of the total cell voltage, which makes the position of their mid-point on the X-axis relatively uncritical. The same partial voltage can also be tapped off if the voltage electrodes 7 and 8 are shifted along points on their equipotential lines 17, 18, respectively chosen so that they are no longer in the area of the greatest current density.

Figure 3:
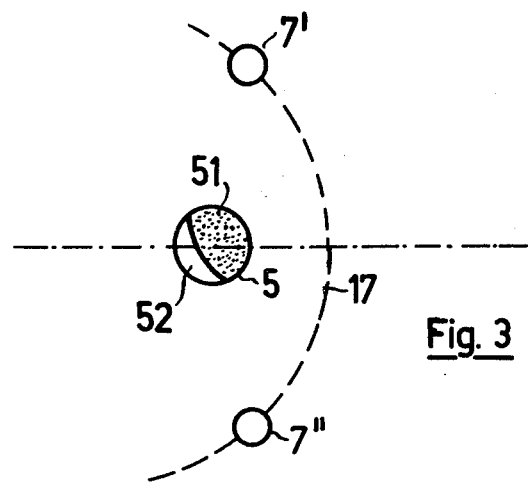
FIG. 3 illustrates half of a measuring cell.

FIG. 3 shows half a measuring cell with current electrode 5 and one voltage electrode, consisting of two parallel connected electrodes 7' and 7'', on the common equipotential line 17. Because of non-conductive encrustation of current electrode 5, the mid-point of the current outlet shifts from 51 to 52. Thus, the distance to the electrode 7' increases, but the distance to the electrode 7'' decreases. The voltage tap-off thus corresponds to that of a totally pollution free electrode 5. As a result of the parallel connection of electrodes 7' and 7'' an equilizing current now flows which can bring about a secondary polarization. This disadvantage is minimized by the electrode arrangement explained above using the effect which is interesting from the point of view of measurement technology and could be reduced still further by raising the measurement frequency.

Figure 4:
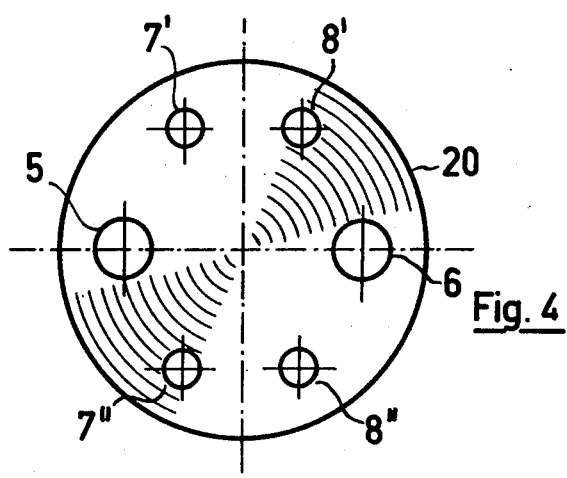
FIG. 4 is a plan view of an embodiment of the present invention.
Figure 5:
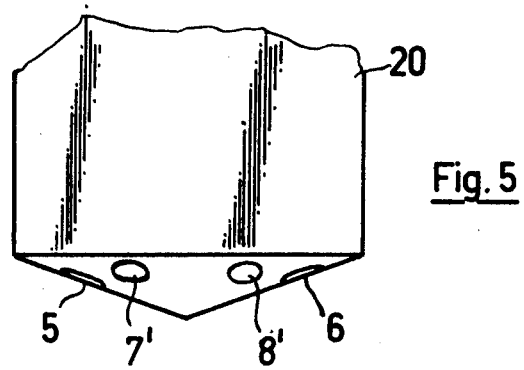
FIG. 5 is an elevation of the same embodiment.

FIGS. 4 ans 5 show an embodiment of the four electrode type measuring cell utilizing partial electrodes 7', 7" and 8', 8" associated respectively with the current electrodes 5 and 6. The electrodes lie in a plane at the bottom of a shaft member 20 and have circular surfaces. To permit the removal of air bubbles the surface of the shaft member containing the electrodes is slightly chamfered in a cone or hemisphere shape thereby changing the end surface shape of the electrodes, which, in addition, enables the cell constants to be corrected by a few percent, depending on the extent of the chamfering.

An advantageous development is provided by the use for example of four partial electrodes per voltage tap-off, arranged on the same equipotential line and producing a further improved voltage information, if the location of the current outlet on the current electrode shifts from the center.

While I have shown and described only one embodiment in accordance with the present invention, it is understood that the same is not llimited thereto but is susceptible of numerous changes and modifications as known to those skilled in the art, and I therefore do not wish to be limited to the details shown and described herein but intend to cover all such changes and modifications as are encompassed by the scope of the appended claims.

I claim:
1. In a cell for measurement of electrical conductivity of liquids having two current electrodes with a defined spacing therebetween and voltage electrode means for providing a voltage tap-off according to the four electrode measuring technique, the improvement wherein the voltage electrode means comprises at least two voltage electrodes associated with each current electrode, the at least two voltage electrodes being electrically connected in parallel for providing a voltage tap-off and being disposed along an equipotential line around a current electrode at positions on the equipotential line.

2. A cell according to claim 1, wherein the voltage and current electrodes form circular surfaces and are arranged in one plane.

3. A cell according to claim 2, further comprising a shaft member containing the voltage and current electrodes.

4. A cell according to claim 1, wherein the end surface of the voltage and current electrodes is a portion of one of a hemisphere and a cone.

5. A cell according to claim 4, further comprising a shaft member containing the voltage and current electrodes, the end surface of the shaft member being one of a hemisphere and a cone.

6. A cell according to claim 4, wherein the cell constant is variable in accordance with the size of curvature of one of the hemisphere and cone.

7. A cell according to claim 5, wherein the cell constant is variable in accordance with the size of curvature of one of the hemisphere and cone.

8. A cell according to claim 1, further comprising a high-Z amplifier means having an input coupled to the voltage electrode means and an output coupled to the current electrode means.

9. A cell according to claim 1, wherein the voltage and current electrodes have end surfaces coextensive with the end of a shaft of an insulating body.

10. A cell according to claim 9, wherein the end surfaces of the voltage and current electrodes are in the form of one of a plane, a portion of a hemisphere and a portion of a cone.

* * * * *